United States Patent
Shin et al.

(10) Patent No.: US 9,924,927 B2
(45) Date of Patent: Mar. 27, 2018

(54) METHOD AND APPARATUS FOR VIDEO INTERPRETATION OF CAROTID INTIMA-MEDIA THICKNESS

(71) Applicant: Arizona Board of Regents on Behalf of Arizona State University, Scottsdale, AZ (US)

(72) Inventors: Jae Yul Shin, Phoenix, AZ (US); Nima Tajbakhsh, Tempe, AZ (US); Jianming Liang, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/049,935

(22) Filed: Feb. 22, 2016

(65) Prior Publication Data
US 2017/0238909 A1    Aug. 24, 2017

(51) Int. Cl.
*A61B 8/00*   (2006.01)
*A61B 8/08*   (2006.01)
(Continued)

(52) U.S. Cl.
CPC .......... *A61B 8/5284* (2013.01); *A61B 5/0402* (2013.01); *A61B 5/0456* (2013.01);
(Continued)

(58) Field of Classification Search
CPC .. A61B 8/5223; A61B 5/02007; A61B 8/0891
See application file for complete search history.

(56) References Cited

U.S. PATENT DOCUMENTS

| | | | |
|---|---|---|---|
| 2004/0260682 A1* | 12/2004 | Herley | G06K 9/00496 |
| 2005/0249328 A1* | 11/2005 | Bruder | A61B 6/032 378/8 |
| 2014/0135627 A1* | 5/2014 | Liang | A61B 5/02007 600/449 |

FOREIGN PATENT DOCUMENTS

WO    WO2015142808    9/2015

OTHER PUBLICATIONS

H. Sharma, R. G. Golla, Y. Zhang, C. B. Kendall, R. T. Hurst, N. Tajbakhsh, and J. Liang, "Ecg-based frame selection and curvature-based roi detection for measuring carotid intima-media thickness," in SPIE Medical Imaging. International Society for Optics and Photonics, 2014, pp. 904016-904016.

(Continued)

*Primary Examiner* — Rajeev Siripurapu
(74) *Attorney, Agent, or Firm* — Schwabe, Williamson & Wyatt, P.C.

(57) ABSTRACT

A system for automatically determining a thickness of a wall of an artery of a subject includes an ECG monitoring device that captures an electrocardiogram (ECG) signal from the subject, and an ultrasound video imaging device, coupled to the ECG monitoring device, that receives the ECG signal from the ECG monitoring device, and captures a corresponding ultrasound video of the wall of the artery of the subject. The system produces a plurality of frames of video comprising the ultrasound video of the wall of the artery of the subject and an image of the ECG signal. A processor is configured to select a subset of the plurality of frames of the ultrasound video based on the image of the (ECG) signal, locate automatically a region of interest (ROI) in each frame of the subset of the plurality of frames of the video using a machine-based artificial neural network and measure auto- (Continued)

matically a thickness of the wall of the artery in each ROI using the machine-based artificial neural network.

32 Claims, 7 Drawing Sheets

(51) Int. Cl.
  *A61B 5/0402* (2006.01)
  *A61B 5/00* (2006.01)
  *A61B 5/0456* (2006.01)
  *A61B 5/107* (2006.01)
  *A61B 5/02* (2006.01)

(52) U.S. Cl.
  CPC ............ *A61B 5/1075* (2013.01); *A61B 5/489* (2013.01); *A61B 5/7267* (2013.01); *A61B 5/7289* (2013.01); *A61B 5/7485* (2013.01); *A61B 8/0891* (2013.01); *A61B 8/469* (2013.01); *A61B 5/02007* (2013.01); *A61B 8/5223* (2013.01)

(56) References Cited

OTHER PUBLICATIONS

X. Zhu, C. B. Kendall, R. T. Hurst, and J. Liang, "A user friendly system for ultrasound carotid intima-media thickness image interpretation," in SPIE Medical Imaging. International Society for Optics and Photonics, 2011, pp. 79681G-79681G.

J. Liang, T. McInerney, and D. Terzopoulos, "United snakes," Medical image analysis, vol. 10, No. 2, pp. 215-233, 2006.

N. Otsu, "A threshold selection method from gray-level histograms," IEEE transactions on systems, man, and cybernetics, vol. 9, issue 1, pp. 62-66, 1979.

International search report (ISR) for PCT application No. PCT/US2015/020908 filed on Mar. 17, 2015.

Shin, J, "A unified framework based on convolutional neural networks for interpreting carotid intima-media thickness videos". Master of Science Thesis. Arizona State University. Apr. 2016.

* cited by examiner

METHOD AND APPARATUS FOR VIDEO INTERPRETATION OF CAROTID INTIMA-MEDIA THICKNESS

BACKGROUND

The subject matter described herein relates to systems and methods for determining carotid artery intima-media thickness (CIMT).

Cardiovascular disease (CVD) is the number one killer in the United States. Nevertheless, CVD is largely preventable. However, the key is to identify at-risk persons before coronary events occur, so that preventive care can be prescribed appropriately. A noninvasive ultrasonography method that has proven to be valuable for predicting individual CVD risk involves determining a person's carotid artery intima-media thickness (CIMT). Interpretation of CIMT ultrasonographic videos involves three manual operations: 1) selection of end-diastolic ultrasonographic frames (EUFs) in each video; 2) localization of a region of interest (ROI) in each selected EUF; and 3) identification of the intima-media boundaries within each ROI to measure CIMT. With reference to FIG. 1, which illustrates a longitudinal view of the common carotid artery of a human subject in an ultrasonographic B-scan image 100, CIMT is defined as the distance between the lumen-intima interface and the media-adventitia interface, measured approximately 1 cm from the carotid bulb on the far wall of the common carotid artery at the end of the diastole. Therefore, interpretation of a CIMT video involves 3 operations: 1) select 3 EUFs in each video (the cardiac cycle indicator shows to where in the cardiac cycle the current frame in the video corresponds); 2) localize an ROI approximately 1 cm distal from the carotid bulb in the selected EUF; and 3) measure the CIMT within the localized ROI.

These three operations, and in particular, the third step of CIMT measurement, are not only tedious and laborious but also subjective to large inter-operator variability if guidelines are not properly followed. These factors have hindered the widespread utilization of CIMT in clinical practice. To overcome this limitation, what is needed is a new system to accelerate CIMT video interpretation through automation of the operations in a novel, unified framework using machine-based artificial neural networks such as convolutional neural networks (CNNs).

SUMMARY

Embodiments of the invention relate to systems, methods and program code for automatically determining a thickness of a wall of an artery of a subject. In one embodiment, an ECG monitoring device captures an electrocardiogram (ECG) signal from the subject, and an ultrasound video imaging device, coupled to the ECG monitoring device, receives the ECG signal from the ECG monitoring device, and also captures a corresponding ultrasound video of the wall of the artery of the subject. The ultrasound video imaging device produces a plurality of frames of video comprising the ultrasound video of the wall of the artery of the subject and, in one embodiment, an image of the ECG signal is integrated in, or displayed on, the frames. A processor coupled to the ultrasound video-imaging device is configured via executable computer program code to select a subset of the plurality of frames of the ultrasound video based on the image of the (ECG) signal. The processor is further configured via the executable computer program code to locate automatically a region of interest (ROI) in each frame of the subset of the plurality of frames of the video and measure automatically a thickness of the wall of the artery in each ROI using a machine-based artificial neural network.

DETAILED DESCRIPTION

Figure 2:
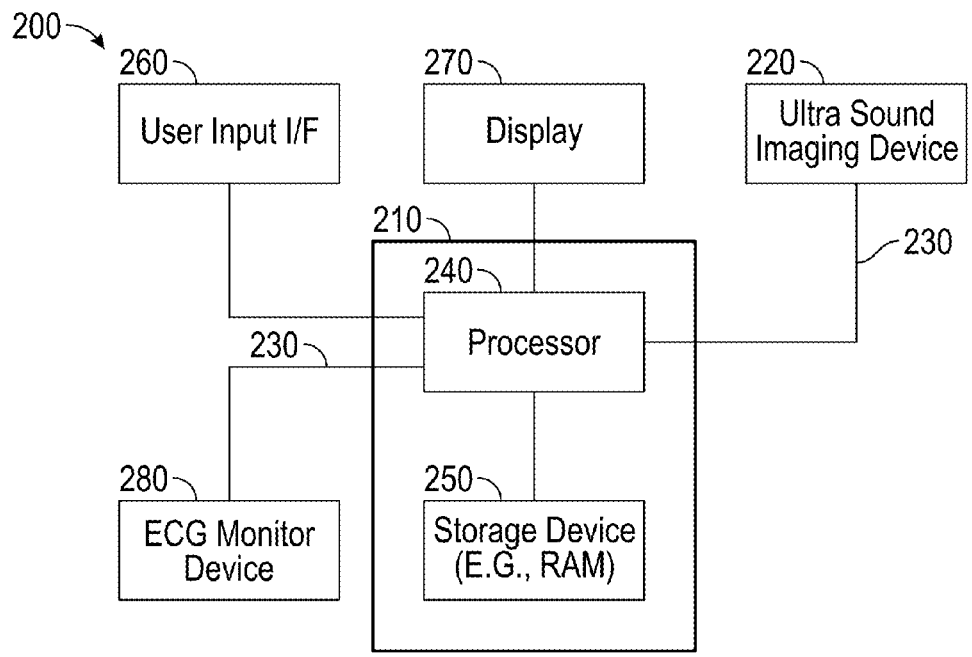
FIG. 2 illustrates a system for implementing embodiments of the invention.
Figure 3:
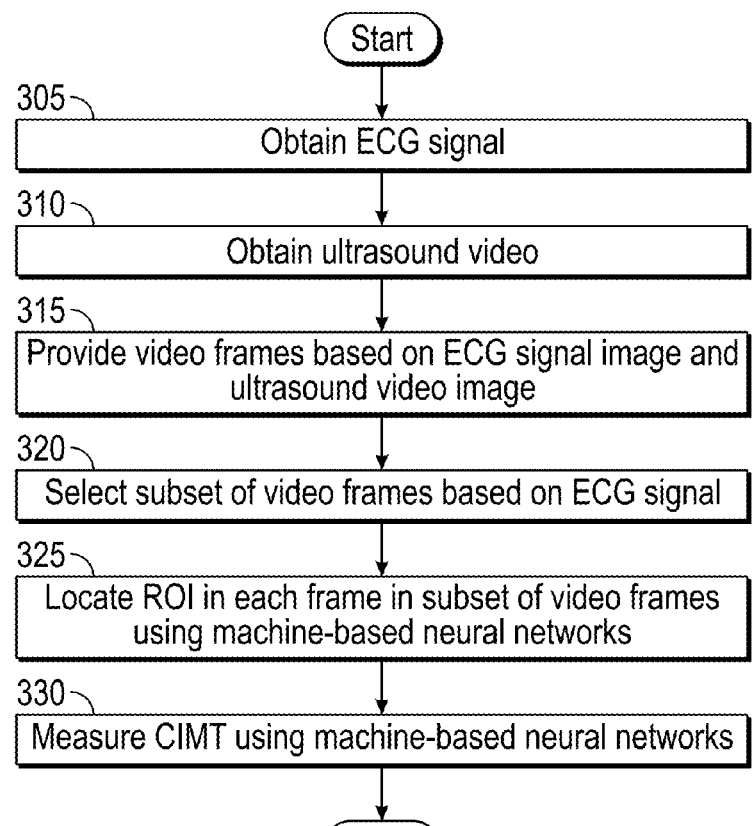
FIG. 3 illustrates a flow chart of a process according to embodiments of the invention.

Embodiments of the invention relate to a system for automatically determining a thickness of a wall of an artery of a subject. The system, as shown in FIG. 2, and with reference to the process shown in the flowchart in FIG. 3, comprises an ECG monitoring device 280 that captures at 305 an electrocardiogram (ECG) signal from the subject. The system further includes an ultrasound video imaging device 220, coupled to the ECG monitoring device 280, in one embodiment, by way of computing device 210, that receives the ECG signal from the ECG monitoring device, and captures at 310 a corresponding ultrasound video of the wall of the artery of the subject. In one embodiment, the ultrasound video imaging device outputs at 315 a plurality of frames of video comprising the ultrasound video of the wall of the artery of the subject and an image of the ECG signal.

In another embodiment, the ECG signal and the ultrasound video are received by a computing device 210 coupled to the ECG monitoring device and ultrasound video imaging device via communication link 230, and a processor 240 combines, stores in storage device 250, and outputs at 315 to display device 270, video frames combining the ultrasound video and an image of the ECG signal.

In one embodiment, the obtained ECG signals are separately encoded in the ultrasound video images in a file, such as a Digital Imaging and Communications in Medicine (DICOM) image file, and they are also synchronized with corresponding frame numbers for the ultrasound video images. (Note: DICOM is also known as NEMA (National Electrical Manufacturers Association) standard PS3, and as ISO standard 12052:2006 "Health informatics—Digital imaging and communication in medicine (DICOM) including workflow and data management"). In one embodiment, the ECG signals are reconstructed from the images when the ECG signal is overlaid on top of, or otherwise combined with, the ultrasound images, if ECG signal was not presented via a separate channel. In another embodiment, the ECG signal is separately presented or available, and does not need to be reconstructed from ultrasound images with which it is combined. It is appreciated that some embodiments may operate with ultrasound video files for which there are no means for separating the ECG signal, for example, video files employing video formats such as AVI, MOV, MP4, etc. It is noted also that ECG signal encoding according to the DICOM standard is in fact not standardized, so each ultrasound video/ECG monitor device manufacturer will use proprietary formatting to store the ECG signals using unique DICOM tags which may present a challenge in interpreting ECG signals. Therefore, one major advantage of embodiments of the present invention is that frame detection can extract any type of ECG signal even if signal cues are missing and/or wrap around to the left on the display screen from the embedded images where separate ECG signals cannot be obtained directly from DICOM video format and without knowing a particular manufacturer's specification for ECG signal encoding format.

A processor 240 of the computing device 210 is then configured at 320 to select a subset of the plurality of frames of the ultrasound video based on the image of the (ECG) signal. In one embodiment, the selection may be accomplished using a machine-based artificial neural network, such as convolutional neural networks. In one embodiment, the processor is configured to select a plurality of end-diastolic ultrasound frames (EUFs) based on corresponding R-waves in a QRS complex in the image of the ECG signal, using the machine-based artificial neural network. Once the subset of video frames is selected based on the ECG signal, the processor is configured at 325 to automatically localize a region of interest (ROI) in each frame of the subset of the plurality of frames of the video using the machine-based artificial neural network, With regard to step 325, in one embodiment, the processor is configured to estimate a location of the ROI in each frame of the subset of the plurality of frames of the video, and a location of a well-known area of the artery of the subject as a contextual constraint, and then refine the estimated location of the ROI given the estimated location of the well-known area of the artery. In one embodiment, the location of the well-known area of the artery is the location of the carotid bulb of a subject's common carotid artery (CCA) and the estimated location of the ROI is approximately 1 centimeter from the carotid bulb on a far wall of the subject's CCA.

Having determined the location of the ROI in each frame in the subset of video frames, the system measures automatically at 330 a thickness of the wall of the artery in each ROI using the machine-based artificial neural network. In particular, the processor is configured to measure automatically a carotid intima-media thickness (CIMT) of the far wall of the carotid artery in each ROI using the machine-based artificial neural network. This measurement is accomplished in one embodiment by first detecting a lumen-intima interface of the wall of the carotid artery, further detecting a media-adventitia interface of the wall of the carotid artery, and then measuring the distance between the lumen-intima interface and the media-adventitia interface to determine the CIMT of the carotid artery.

Figure 1:
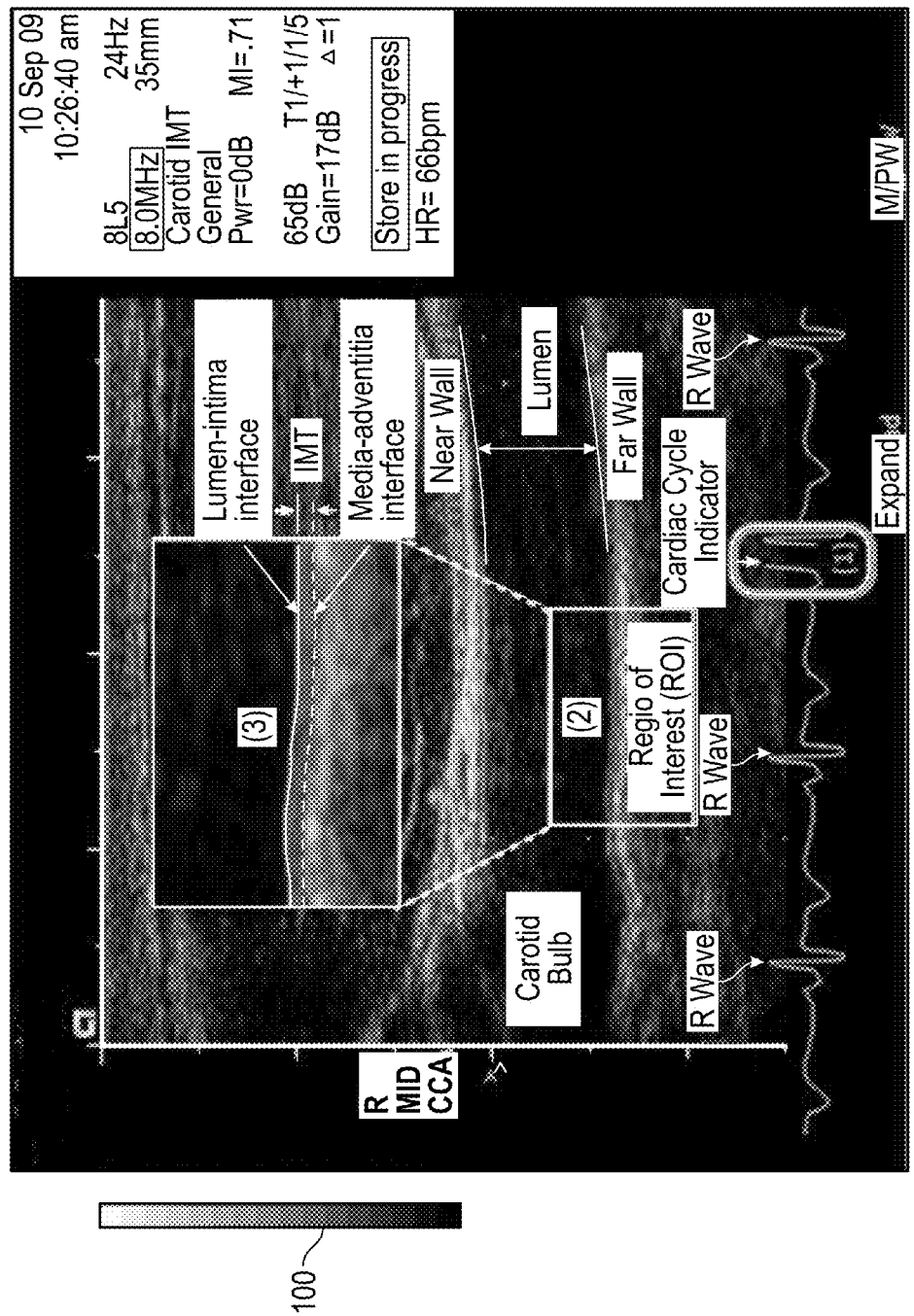
FIG. 1 illustrates a longitudinal view of the common carotid artery of a human subject in an ultrasonographic B-scan image.

In one embodiment, CIMT examinations may be performed with high resolution B-mode ultrasonography using a 15 MHz linear array transducer with fundamental frequency only (such as available from Acuson Sequoia, Mountain View, Calif., USA). The carotid screening protocol begins with scanning up from the lower neck in a transverse manner to the carotid artery and then further to the carotid bulb and to internal and external carotid arteries. The probe is then turned to obtain a longitudinal view of the common carotid artery, as illustrated in FIG. 1. A sonographer optimizes the 2-dimensional images of the lumen-intima and media-adventitia interfaces at the level of the common carotid artery by adjusting overall gain, time gain, compensation, and focus position. After the parameters are adjusted, the sonographer captures two CIMT videos focused on the common carotid artery from at least two optimal angles of incidence. The same procedure may be repeated for the other side of neck, resulting in a total of four CIMT videos for each patient. In one embodiment, the videos are recorded at 24 frames/second and consist of 640×480 pixels of video resolution in the ultrasound images. The pixel spacing is 0.09 mm/pixel along both x and y directions.

Further details of embodiments of the invention that provide a unified solution based on convolutional neural networks (CNNs) for automating the three main tasks in CIMT video interpretation, namely, frame selection, region of interest (ROI) localization, and intima-media thickness measurement, are provided below.

Frame Selection

The first step in automatically determining a thickness of a wall of an artery of a subject involves obtaining an ultrasound video of the wall of the artery of the subject, the ultrasound video comprising a plurality of frames of video, obtaining a corresponding electrocardiogram (ECG) signal from the subject, and then selecting a subset of the plurality of frames of the video based on the corresponding (ECG) signal. In one embodiment, selecting the subset of the plurality of frames of the ultrasound video based on the corresponding ECG signal involves selecting end-diastolic ultrasound frames (EUFs) based on corresponding R-waves in a QRS complex of the ECG signal. In one embodiment, selecting the subset of the plurality of frames of the ultrasound video based on a corresponding electrocardiogram (ECG) signal involves automatically selecting the subset of the plurality of frames of the ultrasound video based on an image of the corresponding electrocardiogram (ECG) signal displayed in the ultrasound video, using a machine-based artificial neural network, such as a convolutional neural network.

In one embodiment, given a CIMT video, the first step in cardiovascular risk assessment selects three EUFs. The CIMT test is routinely performed with ECG, and an operator normally selects the three EUFs on the basis of the ECG signal that is displayed at the bottom of the ultrasonographic frames. Each frame in the CIMT video corresponds to a particular location in the printed ECG signal. To establish this correspondence, as shown in FIG. 1, a black line indicator (cardiac cycle indicator (1)) is displayed on the image of the ECG signal, indicating to where in the cardiac cycle the current video frame corresponds. In routine clinical practice, the operator selects the EUFs so that the corresponding black line indicator coincides with the R wave in the QRS complex of the printed ECG signals.

Figure 4:
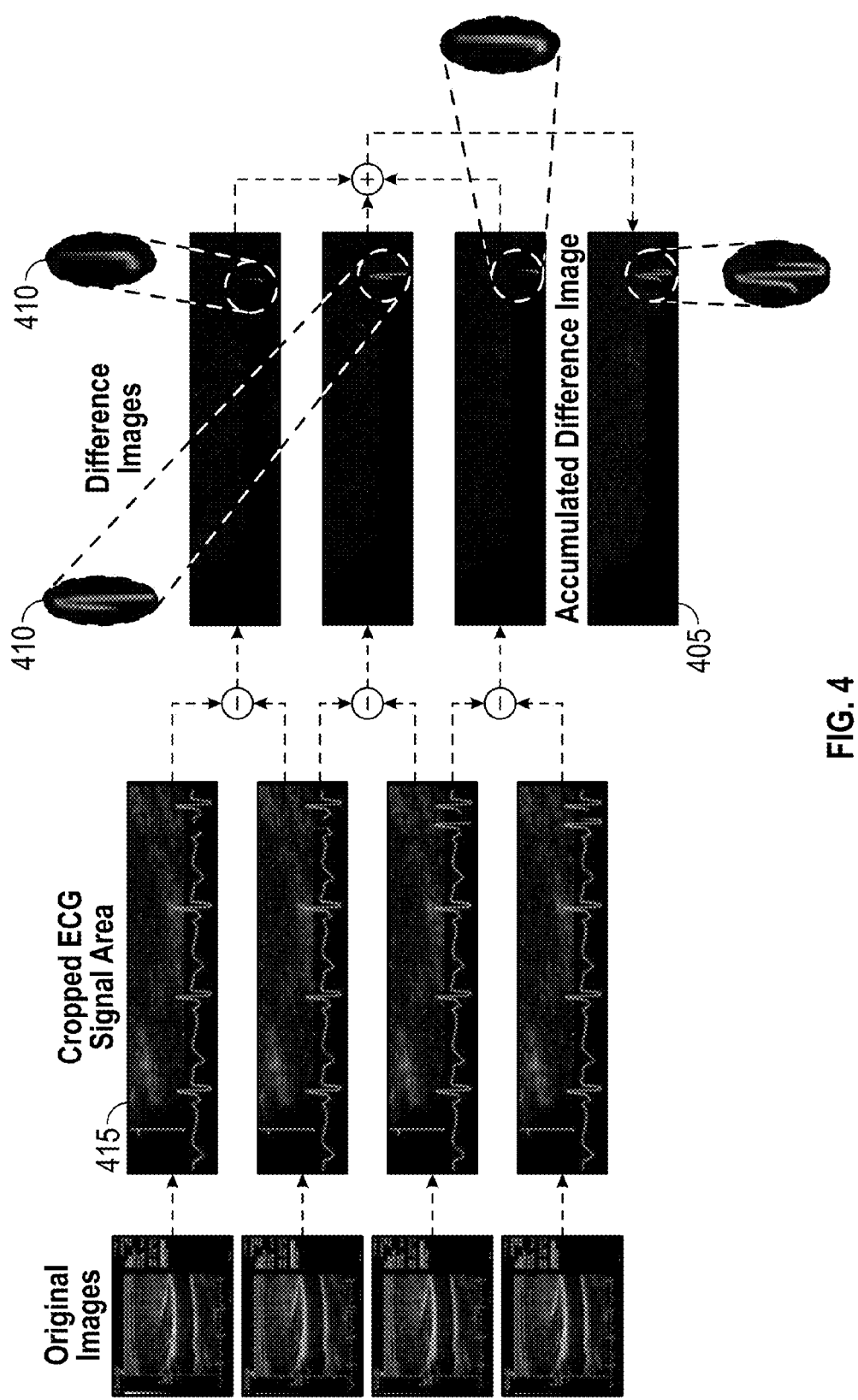
FIG. 4 illustrates accumulated difference images according to an embodiment of the invention.

One embodiment automates the frame selection process by automatically identifying the frames that correspond to the R wave in the QRS complex in the image of ECG signal. According to an embodiment, the segment of the ECG signal that is masked by the black line indicator in the current frame is reconstructed, and then a determination is made as to whether the restored wavelet (that is, the small part of the ECG signal that is reconstructed) resembles the appearance of an R wave or not. For this purpose, and with reference to FIG. 4, accumulated difference images 405 are used to capture the missing wavelets 410 and then a CNN is used to classify these captured wavelets into R wave or non-R wave categories.

Let $I^t$ denote an image sub region selected from the bottom of an ultrasonographic frame 415 (e.g., the bottom 20%) that contains the displayed ECG signal. First, the set of difference images $d^t$ are constructed by subtracting every consecutive pair of images, $dt=|I^t-I^{t+1}|$, and then form accumulated difference images by adding up every 3 neighboring difference images, $$D^t = \Sigma_{i=0}^2 d^{t-i}$$

An accumulated difference image $D^t$ can capture the segment of the ECG signal that is masked by the black line indicator at frame t. Second, the location of the restored wavelet in each accumulated difference image is determined. In one embodiment, this is accomplished by finding the weighted centroid $c=[c_x, c_y]$ of each accumulated difference image $D^t$ as follows:

$$c = \frac{1}{Z_t} \sum_{p \in D^t} D^t(p_x, p_y) \times p$$

where $p=[p_x; p_y]$ is a pixel in the accumulated difference image and $$Z^t = \Sigma_{p \in D^t} D^t(p_x, p_y)$$

is a normalization factor that ensures the weighted centroid stays within the image boundary. After centroids are identified, patches of size 32×32 pixels are extracted around the centroid locations. Specifically, patches with up to 2 pixel translations from each centroid are extracted. In one embodiment, data augmentation is not performed by scaling the patches because doing so would inject label noise in the training set. For instance, a small, restored wavelet may take the appearance of an R wave after expanding, or an R wave may look like a non-R wave after shrinking. Rotation-based patch augmentation is also not performed because it is not expected for the restored wavelets to appear with rotation in the test image patches. After collection, the patches are binarized according to the method described in N. Otsu, "A threshold selection method from gray-level histograms," *Automatica*, vol. 11, no. 285-296, pp. 23-27, 1975. Each binary patch is then labeled as positive if it corresponds to an EUF (or an R wave); otherwise, it is labeled as negative. Basically, given a patch, one embodiment initially determines the accumulated difference image from which the patch is extracted, followed by tracing back to the underlying difference images to check whether they are related to the EUF or not. After the patches are labeled, a stratified set is formed with 96,000 patches to train a CNN for distinguishing between R waves and non-R waves.

Figure 5:
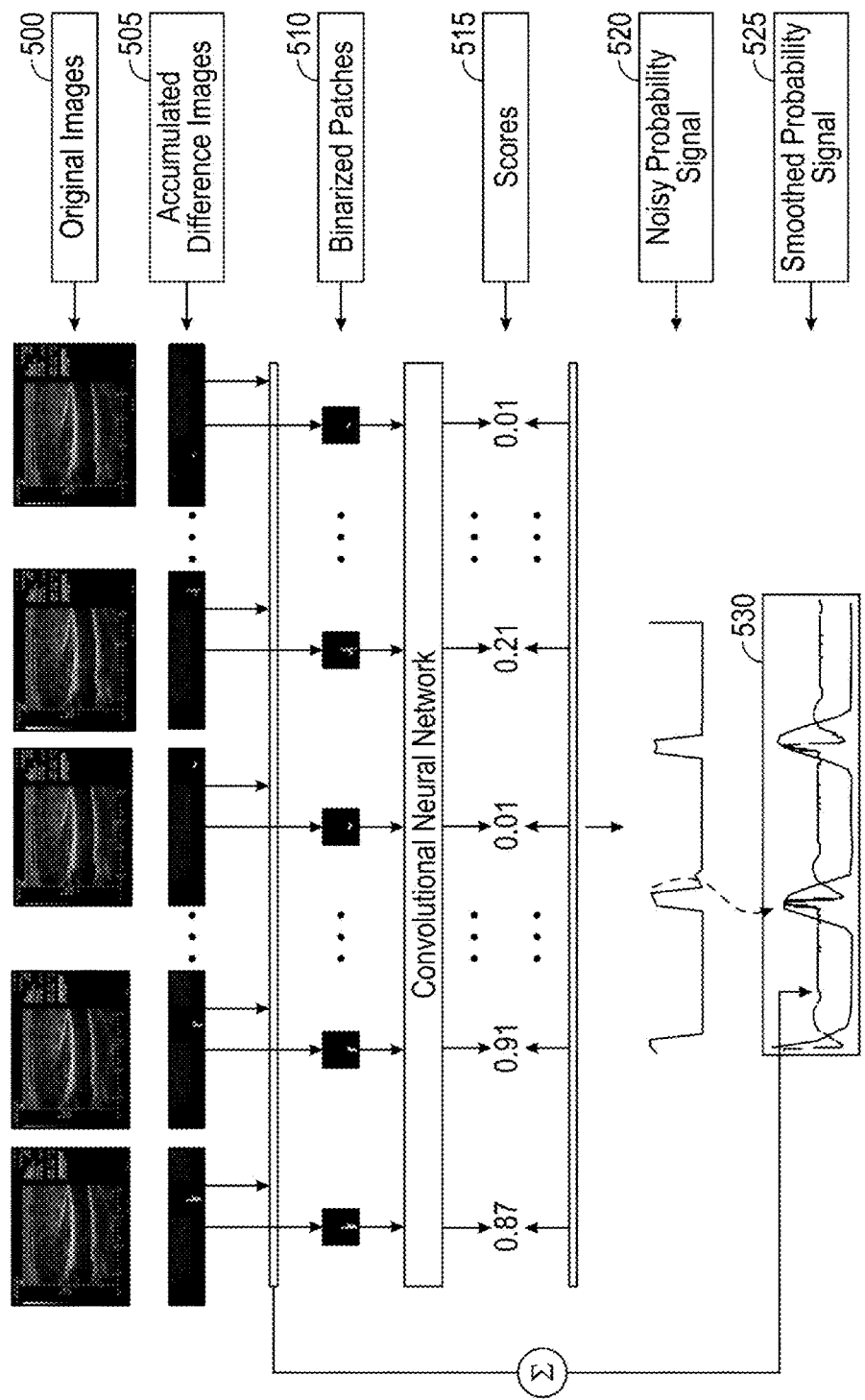
FIG. 5 shows a frame selection system for a test video, according to one embodiment of the invention.

FIG. 5 shows a frame selection system for a test video, according to one embodiment of the invention. An accumulated difference image is computed at 505 for each original image frame 500 in the video. Binarized image patches 510 are then extracted from the weighted centroids of the accumulated difference images. At 515, the probability of each frame being the EUF is measured as the average probabilities assigned by the CNN to the corresponding patches. By concatenating the resulting probabilities for all frames in the video, a noisy probability signal is obtained at 520 whose local maxima indicate the locations of the EUFs. However, the generated probability signals often exhibit abrupt changes, which can cause too many local maxima along the signal. One embodiment, therefore, first smoothed at 525 the probability signal using a Gaussian function and then finds the EUFs by locating the local maxima of the smoothed signals. FIG. 5, for illustration purposes, also shows at 530 the reconstructed ECG signal, which is computed as the average of the accumulated difference images, $$\frac{1}{N} \sum_{t=1}^{N} D^t$$

with N being the number of frames in the video. As seen, the probability of a frame being the EUF reaches a maximum around the R waves of the QRS complexes (as desired) and then smoothly decays as it distances from the R waves. By mapping the locations of the local maxima to the frame numbers, EUFs in the video can be identified.

ROI Localization

ROI localization involves locating automatically a region of interest (ROI) in each frame of the subset of the plurality of frames of the video using a machine-based artificial neural network. One embodiment for ROI localization estimates, simultaneously, a location of the ROI in each frame of the subset of the plurality of frames of the video, and a location of a well-known area of the artery of the subject as a contextual constraint, and then refines the estimated location of the ROI given the estimated location of the well-known area of the artery. As described above, in one embodiment, the location of the well-known area of the artery comprises the location of a carotid bulb of a subject's common carotid artery (CCA), and the estimated location of the ROI is approximately 1 centimeter from the carotid bulb on a far wall of the subject's CCA.

Accurate localization of the ROI can be challenging because, as seen in FIG. 1, no notable differences can be readily observed in image appearance among the ROIs on the far wall of the carotid artery. To overcome this challenge, one embodiment uses the location of the carotid bulb as a contextual constraint. This constraint is chosen for two reasons: 1) the carotid bulb appears as a distinct dark area in the ultrasonographic frame and thus can be uniquely identified; and 2) according to the consensus statement of American Society of Electrocardiography for cardiovascular risk assessment, the ROI should be placed approximately 1 cm from the carotid bulb on the far wall of the common carotid artery. The former motivates the use of the carotid bulb location as a constraint from a technical point of view, and the latter justifies this constraint from a clinical standpoint. See J. Stein, C. Korcarz, R. Hurst, E. Lonn, C. Kendall, E. Mohler, S. Najjar, C. Rembold, and W. Post, "American Society of Echocardiography carotid intima-media thickness task force. Use of carotid ultrasound to identify subclinical vascular disease and evaluate cardiovascular disease risk: a consensus statement from the American Society of Echocardiography carotid intima-media thickness task force. Endorsed by the society for vascular medicine," J Am Soc Echocardiogr, vol. 21, no. 2, pp. 93-111, 2008.

Figure 6:
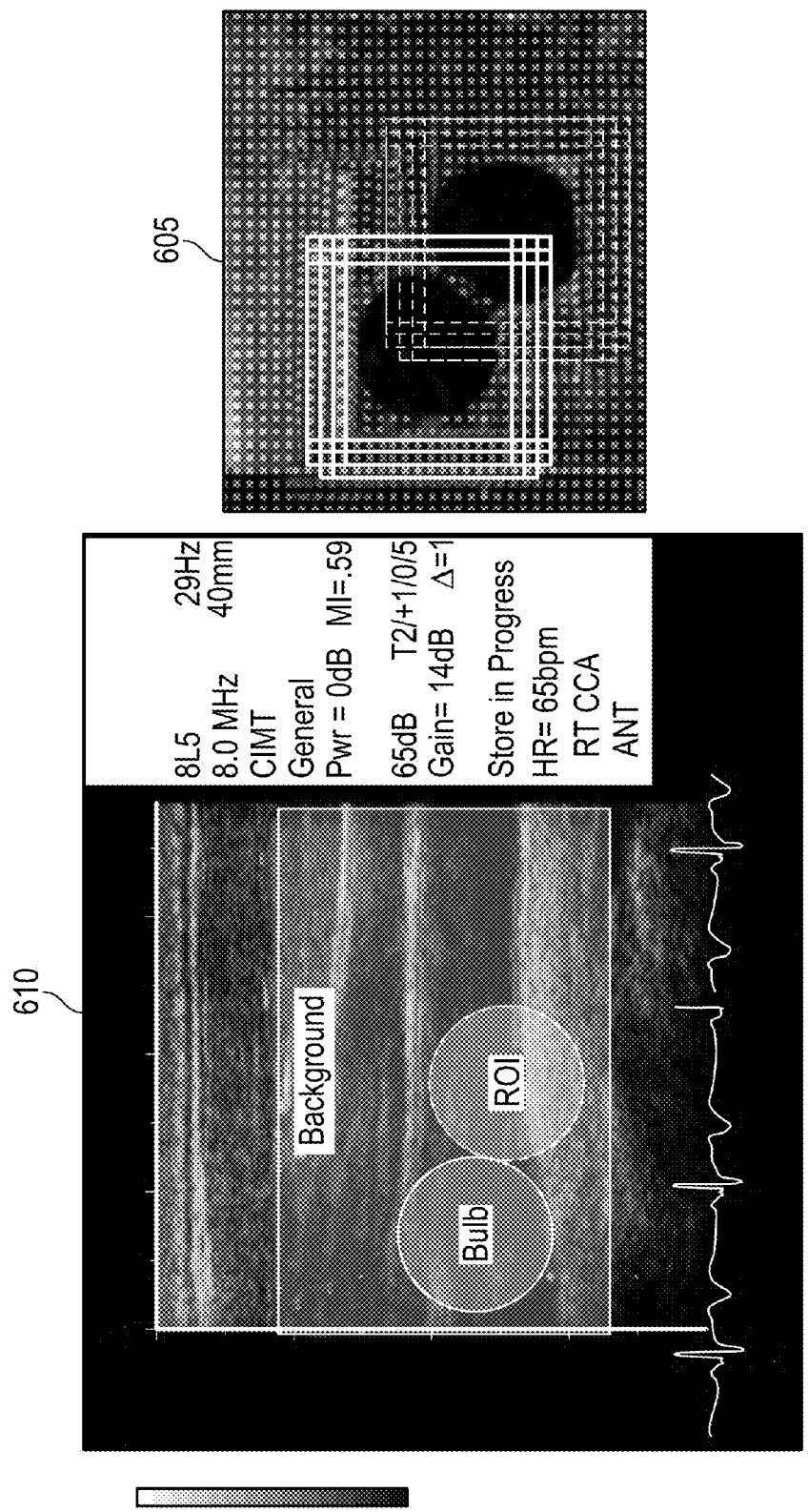
FIG. 6 illustrates aspects of embodiments of the invention related to locating a region of interest (ROI) in each frame of a subset of frames of video.

One embodiment of the invention incorporates this constraint by training a CNN for 3-class classification that simultaneously localizes both the ROI and the carotid bulb and then refines the estimated location of the ROI given the location of the carotid bulb. FIG. 6 shows how the image patches 605 are extracted from a training frame 610. Data augmentation may be performed, by extracting the training patches within a circle around the locations of the carotid bulbs and the ROIs. The background patches are extracted from a grid of points sufficiently far from the locations of the carotid bulbs and the ROIs. Of note, the described translation-based data augmentation is sufficient for this application given a database that provides a relatively large number of training EUFs, from which a large set of training patches can be collected. After the patches are collected, a stratified training set is formed, in one embodiment, with approximately 410,000 patches, to train a CNN for constrained ROI localization.

Figure 7:
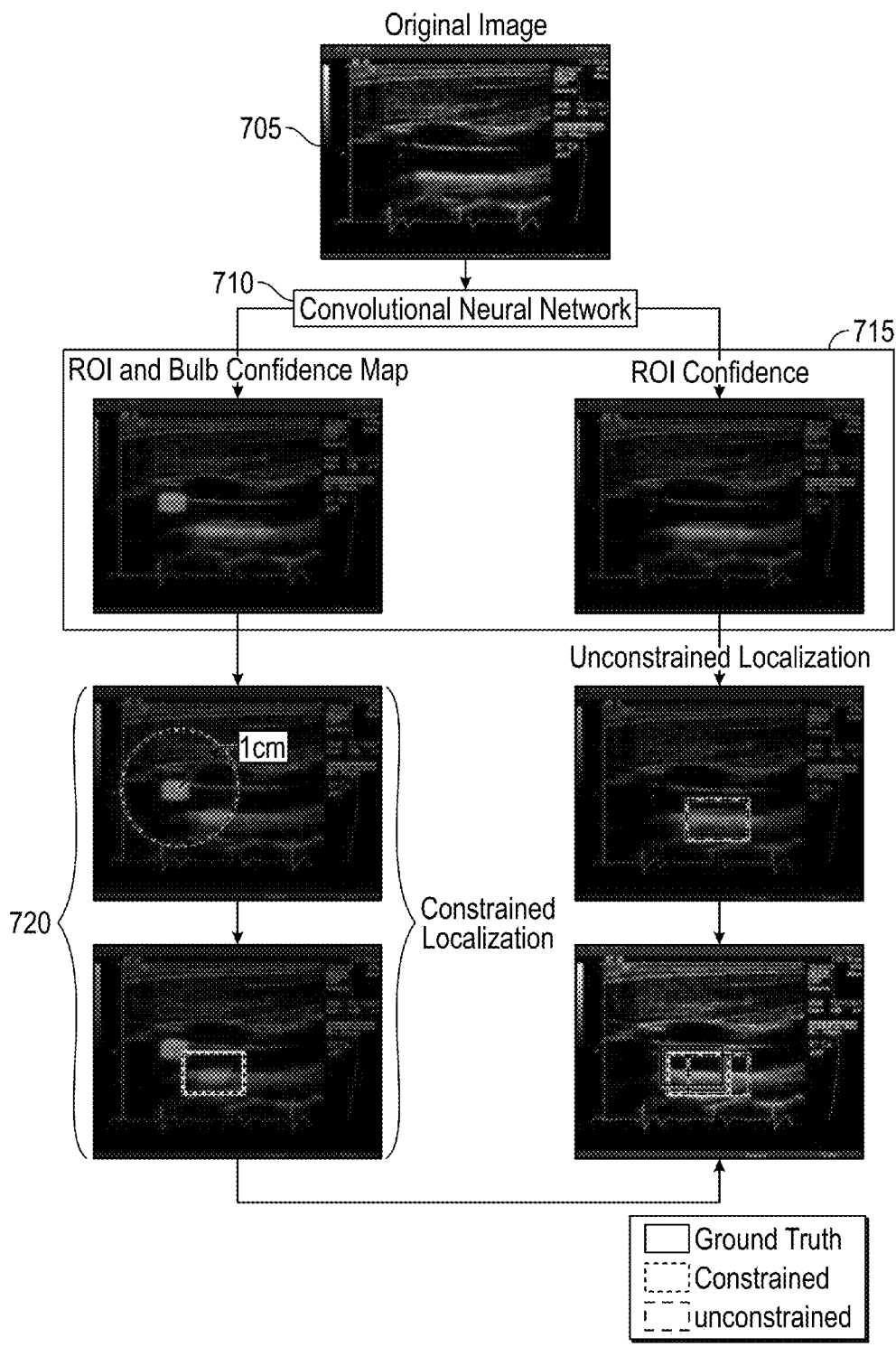
FIG. 7 illustrates aspects of embodiments of the invention related to locating a region of interest (ROI) in each frame of a subset of frames of video.

Referring to FIG. 7, the trained CNN is applied at 710 during a test stage to all the pixels in an EUF 705, generating two confidence maps at 715 with the same size as the EUF, one confidence map showing the probability of a pixel being the carotid bulb, and the other confidence map showing the probability of a pixel being the ROI. One way to localize the ROI is to find the center of the largest connected component within the ROI confidence map without considering the detected location of the carotid bulb. However, this naive approach may fail to accurately localize the ROI. For instance, a long-tail connected component along the far wall of the carotid artery may cause substantial ROI localization error. To compound the problem, the largest connected component of the ROI confidence map may appear far from the actual location of the ROI, resulting in a complete detection failure. To overcome these limitations, one embodiment constraints the ROI location $l_{roi}$ by the location of the carotid bulb $l_{cb}$ as shown at 720. For this purpose, the embodiment determines the location of the carotid bulb as the centroid of the largest connected component within the first confidence map and then localizes the ROI using the following formula:

$$l_{roi} = \frac{\sum_{p \in C*} M(p) \cdot p \cdot I(p)}{\sum_{p \in C*} M(p) \cdot I(p)}$$

where M denotes the confidence map of being the ROI, C* is the largest connected component in M that is nearest to the carotid bulb, and I(p) is an indicator function for pixel $p=[p_x, p_y]$ that is defined as:

$$I(p) = \begin{cases} 1, & \text{if } \|p - l_{cb}\| < 1 \text{ cm} \\ 0, & \text{otherwise} \end{cases}$$

Basically, the indicator function excludes the pixels located farther than 1 cm from the carotid bulb location. This choice of the distance threshold is motivated by the fact that the ROI is located within 1 cm to the right of the carotid bulb. FIG. 7 illustrates how the location of the carotid bulb as a contextual clue improves the accuracy of ROI localization.

Intima-Media Thickness Measurement

The third main step of embodiments of the invention involves measuring automatically the thickness of the wall of the artery in each ROI using the machine-based artificial neural network. In one embodiment, this involves measuring automatically a carotid intima-media thickness (CIMT) of a wall of a carotid artery in each ROI using the machine-based artificial neural network. In particular, measuring the CIMT of the wall of the carotid artery comprises detecting a lumen-intima interface of the wall of the carotid artery, detecting a media-adventitia interface of the wall of the carotid artery, and then measuring a distance between the lumen-intima interface and the media-adventitia interface to determine the CIMT of the carotid artery.

To automatically measure intima-media thickness, the lumen-intima and media-adventitia interfaces of the carotid artery are first detected within the ROI. Although the lumen-intima interface is relatively easy to detect, the detection of the media-adventitia interface is more challenging, because of the faint image gradients around its boundary. One embodiment formulates this interface segmentation problem as a 3-class classification task where the goal is to classify each pixel within the ROI into 3 categories: 1) a pixel on the lumen-intima interface, 2) a pixel on the media-adventitia interface, and 3) a background pixel.

Figure 8:
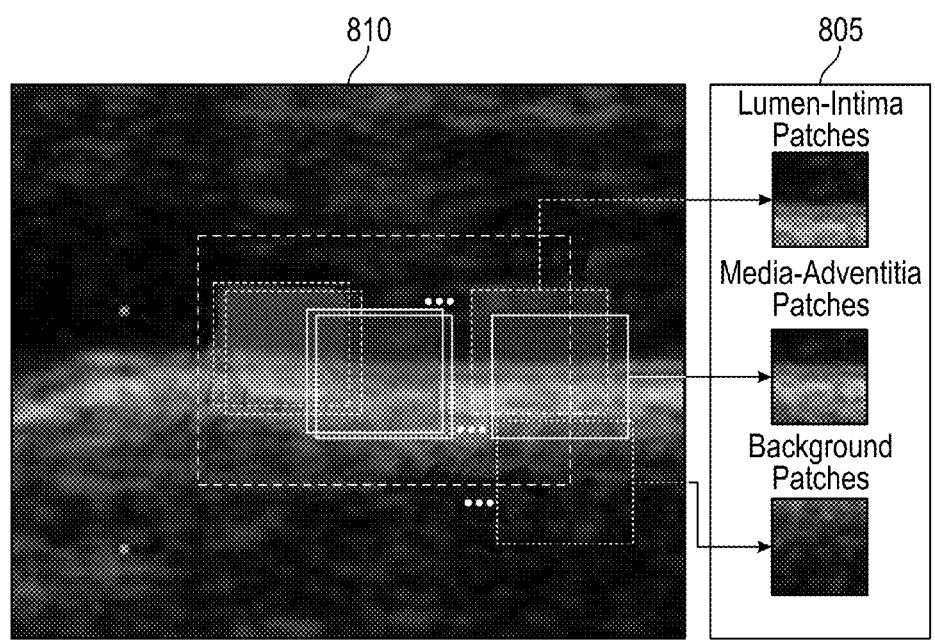
FIG. 8 illustrates aspects of embodiments of the invention related to measuring a thickness of the wall of the artery in a region of interest (ROI).

One embodiment of the invention uses a 3-way CNN to segment the lumen-intima and media-adventitia interfaces. To train the CNN, image patches are collected from the lumen-intima interface and media-adventitia interface, as well as from other random locations far from the desired interfaces. FIG. 8 shows how the training patches are collected at 805 from one ROI 810. In one embodiment, data augmentation is not performed for positive patches because ROIs of 92×60 pixels allow for collecting a large number of patches around the lumen-intima and media-adventitia interfaces. Furthermore, given the relatively small distance between the two interfaces, translation-based data augmentation would inject a large amount of label noise in the training set, which would negatively impact the convergence and the overall performance of the CNN. When the patches are collected, a stratified training set is formed, according to one embodiment, with approximately 380,000 patches, to train a 3-way CNN for interface segmentation.

Figure 9:
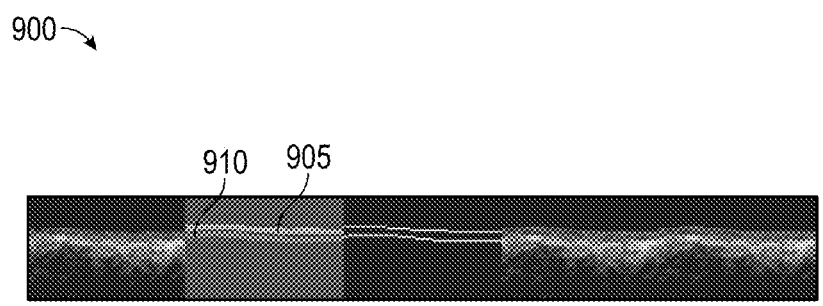
FIG. 9 illustrates aspects of embodiments of the invention related to measuring a thickness of the wall of the artery in a region of interest (ROI).

FIG. 9 illustrates how a system according to an embodiment of the invention measures intima-media thickness in a test ROI 900. 900(*a*) shows test region of interest. At 900(*b*), a trained CNN generates a confidence map where the line 905 and the line 910 indicate the likelihood of lumen-intima interface and a media-adventitia interface, respectively. 900(*c*) illustrates the thick probability band around each interface being thinned by selecting the largest probability for each interface in each column, and 900(*d*) illustrates the step-like boundaries being refined through 2 open snakes. At 900(*e*), a ground truth is made as the consensus of two experts.

The trained CNN is applied to a given test ROI in a convolutional manner, generating two confidence maps with the same size as the ROI. The first confidence map shows the probability of a pixel being on the lumen-intima interface; the second confidence map shows the probability of a pixel being on the media-adventitia interface. The two confidence maps are shown in FIG. 9 where the lines 905 and 910 indicate the likelihood of being the lumen-intima interface and the media-adventitia interface, respectively. A relatively thick high-probability band is apparent along each interface, which hinders the accurate measurement of intima-media thickness. To thin the detected interfaces, the confidence map is scanned, column-by-column, searching for the rows with the maximum response for each of the two interfaces. By doing so, one embodiment obtains a 1-pixel-thick boundary with a step-like shape around each interface as shown in FIG. 9 at 900(*c*). To further refine the boundaries, according to one embodiment, two active contour models (a.k.a., snakes, as described in J. Liang, T. McInerney, and D. Terzopoulos, "United snakes," *Medical image analysis*, vol. 10, no. 2, pp. 215-233, 2006) are employed, one for the lumen-intima interface and one for the media-adventitia interface. The open snakes are initialized with the current step-like boundaries and then deform solely based on the probability maps generated by the CNN rather than the original image content. $900(d)$ shows the converged snakes for the test ROI. In one embodiment, intima-media thickness is determined as the average of vertical distance between the 2 open snakes.

Returning to FIG. 2, it shows a generalized embodiment of an illustrative system 200 via which CIMT can be determined according embodiments of the invention. As shown, the illustrative system 200 includes a computing device 210 and an ultrasound imaging device 220. The system further includes an electrocardiogram (ECG) monitoring device 280. Computing device 210 can be any suitable computing device for providing access to the video frames from device 220 and ECG signal from device 280, such as a processor, a computer, a data processing device, or a combination of such devices. For example, embodiments of the invention can be distributed into multiple backend components and multiple frontend components or interfaces. In a more particular example, backend components, such as data collection and data distribution can be performed on ultrasound imaging device 220. Similarly, the graphical user interfaces displayed by the system, such as an interface for displaying ultrasound images, ECG images, and measuring carotid intima-media thickness, can be distributed by one or more computing devices 210.

Ultrasound imaging device 220 can be any suitable imaging device, such as a high resolution B-mode ultrasound imaging device. Alternatively or additionally, any suitable imaging device (e.g., x-ray imaging device, magnetic resonance imaging device, etc.) can be connected to the computing device 210 that is executing image interpretation application code.

More particularly, for example, computing device 210 can be any of a general-purpose device such as a computer or a special purpose device such as a client, a server, etc. Any of these general or special purpose devices can include any suitable components such as a processor (which can be a microprocessor, digital signal processor, a controller, etc.), memory, communication interfaces, display controllers, input devices, etc. For example, client 210 can be implemented as a personal computer, a tablet computing device, a personal data assistant (PDA), a portable email device, a multimedia terminal, a mobile telephone, a gaming device, a set-top box, a television, etc.

In some embodiments, any suitable computer readable media can be used for storing instructions for performing the processes described herein, can be used to determine carotid intima-media thickness, etc. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Referring back to FIG. 2, communications link 230 (and other links described herein) may be any communications links suitable for communicating data between computing device 210, ultrasound imaging device 220, and ECG monitoring device 280, such as network links, dial-up links, wireless links, hard-wired links, any other suitable communications links, or a combination of such links. Computing device 210 enables a user to access features of embodiments of the invention. Computing device 210 may be personal computers, laptop computers, mainframe computers, dumb terminals, data displays, Internet browsers, personal digital assistants ("PDAs"), two-way pagers, wireless terminals, portable telephones, any other suitable access device, or any combination of such devices. Computing device 210, ECG monitoring device 280, and ultrasound imaging device 220 may be located at any suitable location. In one embodiment, computing device 210, ECG monitoring device 280, and ultrasound imaging device 220 may be located within an organization. Alternatively, computing device 210 and ultrasound imaging device 220 may be distributed between multiple organizations.

It should also be noted that computing device 210 can include processor 240, storage device/memory 250, input device 260, and display 270, which may be interconnected. In some embodiments, memory 250 contains a storage device for storing a computer program for controlling processor 240.

Processor 240 uses the computer program to present on display device 270 the image interpretation and the data received through communications link 230 and commands and values transmitted by a user of computing device 210. It should also be noted that data received through communications link 230 or any other communications links may be received from any suitable source. Input device 260 may be a computer keyboard, a mouse, a cursor-controller, dial, switchbank, lever, or any other suitable input. Alternatively, input device 260 may be a finger or stylus used on a touch screen display 270.

Some embodiments may include an application program interface (not shown), or alternatively, the program code may be resident in the memory of computing device 210. In another suitable embodiment, the only distribution to computing device 210 may be a graphical user interface ("GUI") which allows a user to interact with the system resident at, for example, another computing device.

One embodiment may include client-side software, hardware, or both. For example, an embodiment may encompass one or more Web-pages or Web-page portions (e.g., via any suitable encoding, such as Hyper-Text Markup Language ("HTML"), Dynamic Hyper-Text Markup Language ("DHTML"), Extensible Markup Language ("XML"), Java Server Pages ("JSP"), Active Server Pages ("ASP"), Cold Fusion, or any other suitable approaches).

Although the invention has been described and illustrated in the foregoing illustrative embodiments, it is understood that the present disclosure has been made only by way of example, and that numerous changes in the details of implementation of the invention can be made without departing from the spirit and scope of the invention, which is only limited by the claims which follow. Features of the disclosed embodiments can be combined and rearranged in various ways.

What is claimed is:

1. A method for determining a thickness of a wall of an artery of a subject, comprising:
   automatically selecting a subset of a plurality of frames of an ultrasound video of the wall of the artery on the basis of a corresponding R-wave in a QRS complex of an electrocardiogram (ECG) signal of the subject displayed in the plurality of frames, the subset comprising a plurality of end-diastolic ultrasound frames (EUFs), using a machine-based artificial neural network;

locating automatically a region of interest (ROI) in each frame in the subset using the machine-based artificial neural network; and measuring automatically a thickness of the wall of the artery in each ROI using the machine-based artificial neural network, wherein locating automatically the ROI in each frame in the subset of the plurality of frames of the ultrasound video of the wall of the artery, using a machine-based artificial neural network, comprises:

estimating, simultaneously, the location of the ROI in each frame of the subset, and a location of a carotid bulb of the subject's common carotid artery (CCA) as a contextual constraint comprises extracting image patches from each frame in the subset;

extracting training patches centered around the locations of the carotid bulb and the ROI in each image patch;

extracting background patches from a grid of points away from the locations of the carotid bulb and the ROI in each image patch; and labeling and supplying the image patches, training patches, and background patches to the machine-based artificial neural network to train the machine-based artificial neural network.

2. The method of claim 1, wherein selecting the plurality of EUFs comprises:

obtaining a portion of the ECG signal that is referenced by a cardiac cycle indicator for each of the plurality of frames;

determining whether the portion of the ECG signal is the corresponding R-wave in the QRS complex of the ECG signal for each of the plurality of frames;

accumulating the portions of the ECG signal that correspond to the R-wave in the QRS complex of the ECG signal and the portions of the ECG signal that do not correspond to the R-wave in the QRS complex of the ECG signal; and classifying the portions of the ECG signal that correspond to the R-wave in the QRS complex of the ECG signal into a first category and classifying the portions of the ECG signal that do not correspond to the R-wave in the QRS complex of the ECG signal into a second category, using the machine-based artificial neural network.

3. The method of claim 2, wherein accumulating the portions of the ECG signal that correspond to the R-wave in the QRS complex of the ECG signal and the portions of the ECG signal that do not correspond to the R-wave in the QRS complex of the ECG signal comprises accumulating the portions in difference images of the plurality of frames.

4. The method of claim 3, wherein accumulating the portions in difference images of the plurality of frames comprises:

identifying an image sub region for the plurality of frames in which the ECG signal is displayed;

selecting the image sub region in each of the plurality of frames; and accumulating the portions in difference images of the plurality of frames, comprising:

subtracting every consecutive pair of selected image sub regions to create a difference image; and summing every three neighboring difference images to create an accumulated difference image.

5. The method of claim 4, further comprising:

calculating a weighted centroid for each accumulated difference image;

extracting a patch of n×n pixels centered around the weighted centroid for each accumulated difference image;

binarize the patches;

label each patch as positive that corresponds to an R-wave in the QRS complex of the ECG signal;

label each patch as negative that does not correspond to an R-wave in the QRS complex of the ECG signal.

6. The method of claim 5, further comprising:

supplying the patches labeled as positive and the patches labeled as negative to the machine-based artificial neural network to train the machine-based artificial neural network to distinguish between portions of the ECG signal that correspond to the R-wave in the QRS complex of the ECG signal and portions of the ECG signal that do not correspond to the R-wave in the QRS complex of the ECG signal.

7. The method of claim 6, further comprising:

supplying the patches to the trained machine-based artificial neural network;

calculating a probability for each frame being an EUF as an average of probabilities assigned by the machine-based artificial neural network to the corresponding patches;

concatenating the probabilities for all frames to obtain a noisy probability signal;

smoothing the noisy probability signal using a Gaussian function; and locating a local maxima of the smoothed probability signal to locate the EUFs.

8. The method of claim 1, wherein locating automatically a region of interest (ROI) in each frame in the subset of the plurality of frames of the ultrasound video of the wall of the artery, using a machine-based artificial neural network, further comprises:

refining the estimated location of the ROI given the estimated location of the ROI is approximately 1 centimeter from the carotid bulb on a far wall of the subject's CCA.

9. The method of claim 1, further comprising training the machine-based artificial neural network for 3-class classification to perform the estimating, simultaneously, of the location of the ROI in each frame of the subset, and the location of a carotid bulb of the subject's common carotid artery (CCA) as the contextual constraint, and refining the estimated location of the ROI given the estimated location of the ROI is approximately 1 centimeter from the carotid bulb on the far wall of the subject's CCA.

10. The method of claim 1, further comprising:

applying the trained machine-based artificial neural network to all pixels in an EUF;

generating a first confidence map showing a probability of a pixel being located in the carotid bulb;

generating a second confidence map showing a probability of a pixel being located in the ROI; and locating the ROI in the frame by finding a center of a largest connected component in the second confidence map, as constrained by the location of the carotid bulb based on the first confidence map.

11. The method of claim 1, further comprising:

applying the trained machine-based artificial neural network to all pixels in an EUF;

generating a first confidence map showing a probability of a pixel being located in the carotid bulb;
generating a second confidence map showing a probability of a pixel being located in the ROI;
locating the carotid bulb as a centroid of a largest connected component in the first confidence map; and
locating the ROI in the frame, as constrained by the location of the carotid bulb based on the first confidence map.

12. The method of claim 1, wherein measuring automatically a thickness of the wall of the artery in each ROI using the machine-based artificial neural network, comprises:
measuring automatically a carotid intima-media thickness (CIMT) of a wall of a carotid artery in each ROI using the machine-based artificial neural network, and wherein measuring automatically the CIMT of the wall of the carotid artery comprises:
detecting a lumen-intima interface of the wall of the carotid artery and a media-adventitia interface of the wall of the carotid artery; and
measuring a distance between the lumen-intima interface and the media-adventitia interface to determine the CIMT of the carotid artery.

13. The method of claim 12, wherein the machine-based artificial neural network is a three-way convolutional neural network (CNN), and wherein detecting the lumen-intima interface of the wall of the carotid artery and the media-adventitia interface of the wall of the carotid artery comprises the three-way CNN segmenting the lumen-intima interface of the wall of the carotid artery and the media-adventitia interface of the wall of the carotid artery.

14. The method of claim 4, further comprising training the three-way CNN, comprising:
collecting image patches from the lumen-intima interface and the media-adventitia interface;
collecting image patches from random locations;
creating a stratified training set of image patches from the collected images patches of the lumen-intima interface and the media-adventitia interface and from the collected images patches of the random locations; and
labeling and supplying the training set to the three-way CNN to train the three-way CNN.

15. The method of claim 14, further comprising:
generating a first confidence map with the three-way CNN that shows the probability of a pixel being on the lumen-intima interface;
generating a second confidence map with the three-way CNN that shows the probability of a pixel being on the media-adventitia interface;
searching each confidence map for rows with a maximum response for each of the lumen-intima interface and the media-adventitia interface, thereby obtaining an n-pixel thick boundary for the lumen-intima interface and an n-pixel thick boundary for the media-adventitia interface.

16. The method of claim 15, further comprising refining the boundaries using two active contour models, the two active contour models creating two open snakes, wherein the refining comprises:
initializing the two open snakes, one for each n-pixel thick boundary for the lumen-intima interface and the media-adventitia interface;
deforming the two open snakes based on a probability map generated by the three-way CNN; and
determining intima-media thickness as an average of a vertical distance between the two open snakes.

17. A method for determining a thickness of a wall of an artery of a subject, comprising:
automatically selecting a subset of a plurality of frames of an ultrasound video of the wall of the artery on the basis of a corresponding R-wave in a QRS complex of an electrocardiogram (ECG) signal of the subject displayed in the plurality of frames, the subset comprising a plurality of end-diastolic ultrasound frames (EUFs), using a machine-based artificial neural network, wherein selecting the plurality of EUFs comprises:
obtaining a portion of the ECG signal that is referenced by a cardiac cycle indicator for each of the plurality of frames;
determining whether the portion of the ECG signal is the corresponding R-wave in the QRS complex of the ECG signal for each of the plurality of frames;
accumulating the portions of the ECG signal that correspond to the R-wave in the QRS complex of the ECG signal and the portions of the ECG signal that do not correspond to the R-wave in the QRS complex of the ECG signal by accumulating the portions in difference images of the plurality of frames which comprises
identifying an image sub region for the plurality of frames in which the ECG signal is displayed;
selecting the image sub region in each of the plurality of frames; and
accumulating the portions in difference images of the plurality of frames by subtracting every consecutive pair of selected image sub regions to create a difference image; and summing every three neighboring difference images to create an accumulated difference image;
classifying the portions of the ECG signal that correspond to the R-wave in the QRS complex of the ECG signal into a first category and classifying the portions of the ECG signal that do not correspond to the R-wave in the QRS complex of the ECG signal into a second category, using the machine-based artificial neural network;
locating automatically a region of interest (ROI) in each frame in the subset using the machine-based artificial neural network; and
measuring automatically a thickness of the wall of the artery in each ROI using the machine-based artificial neural network.

18. The method of claim 17, further comprising:
calculating a weighted centroid for each accumulated difference image;
extracting a patch of n×n pixels centered around the weighted centroid for each accumulated difference image;
binarize the patches;
label each patch as positive that corresponds to an R-wave in the QRS complex of the ECG signal;
label each patch as negative that does not correspond to an R-wave in the QRS complex of the ECG signal.

19. The method of claim 18, further comprising:
supplying the patches labeled as positive and the patches labeled as negative to the machine-based artificial neural network to train the machine-based artificial neural network to distinguish between portions of the ECG signal that correspond to the R-wave in the QRS complex of the ECG signal and portions of the ECG signal that do not correspond to the R-wave in the QRS complex of the ECG signal.

20. The method of claim 19, further comprising:
supplying the patches to the trained machine-based artificial neural network;
calculating a probability for each frame being an EUF as an average of probabilities assigned by the machine-based artificial neural network to the corresponding patches;
concatenating the probabilities for all frames to obtain a noisy probability signal; smoothing the noisy probability signal using a Gaussian function; and
locating a local maxima of the smoothed probability signal to locate the EUFs.

21. The method of claim 17, wherein locating automatically a region of interest (ROI) in each frame in the subset of the plurality of frames of the ultrasound video of the wall of the artery, using a machine-based artificial neural network, comprises:
estimating, simultaneously, the location of the ROI in each frame of the subset, and a location of a carotid bulb of the subject's common carotid artery (CCA) as a contextual constraint; and
refining the estimated location of the ROI given the estimated location of the ROI is approximately 1 centimeter from the carotid bulb on a far wall of the subject's CCA.

22. The method of claim 21, further comprising training the machine-based artificial neural network for 3-class classification to perform the estimating, simultaneously, of the location of the ROI in each frame of the subset, and the location of a carotid bulb of the subject's common carotid artery (CCA) as the contextual constraint, and refining the estimated location of the ROI given the estimated location of the ROI is approximately 1 centimeter from the carotid bulb on the far wall of the subject's CCA.

23. The method of claim 21, wherein estimating, simultaneously, the location of the ROI in each frame of the subset, and a location of a carotid bulb of the subject's common carotid artery (CCA) as a contextual constraint, comprises:
extracting image patches from each frame in the subset;
extracting training patches centered around the locations of the carotid bulb and the ROI in each image patch;
extracting background patches from a grid of points away from the locations of the carotid bulb and the ROI in each image patch; and
labeling and supplying the image patches, training patches, and background patches to the machine-based artificial neural network to train the machine-based artificial neural network.

24. The method of claim 23, further comprising:
applying the trained machine-based artificial neural network to all pixels in an EUF; generating a first confidence map showing a probability of a pixel being located in the carotid bulb;
generating a second confidence map showing a probability of a pixel being located in the ROI; and
locating the ROI in the frame by finding a center of a largest connected component in the second confidence map, as constrained by the location of the carotid bulb based on the first confidence map.

25. The method of claim 23, further comprising:
applying the trained machine-based artificial neural network to all pixels in an EUF;
generating a first confidence map showing a probability of a pixel being located in the carotid bulb;
generating a second confidence map showing a probability of a pixel being located in the ROI;
locating the carotid bulb as a centroid of a largest connected component in the first confidence map; and
locating the ROI in the frame, as constrained by the location of the carotid bulb based on the first confidence map.

26. The method of claim 17, wherein measuring automatically a thickness of the wall of the artery in each ROI using the machine-based artificial neural network, comprises: measuring automatically a carotid intima-media thickness (CIMT) of a wall of a carotid artery in each ROI using the machine-based artificial neural network, and wherein measuring automatically the CIMT of the wall of the carotid artery comprises:
detecting a lumen-intima interface of the wall of the carotid artery and a media-adventitia interface of the wall of the carotid artery; and
measuring a distance between the lumen-intima interface and the media-adventitia interface to determine the CIMT of the carotid artery.

27. The method of claim 26, wherein the machine-based artificial neural network is a three-way convolutional neural network (CNN), and wherein detecting the lumen-intima interface of the wall of the carotid artery and the media-adventitia interface of the wall of the carotid artery comprises the three-way CNN segmenting the lumen-intima interface of the wall of the carotid artery and the media-adventitia interface of the wall of the carotid artery.

28. The method of claim 27, further comprising training the three-way CNN, comprising:
collecting image patches from the lumen-intima interface and the media-adventitia interface;
collecting image patches from random locations;
creating a stratified training set of image patches from the collected images patches of the lumen-intima interface and the media-adventitia interface and from the collected images patches of the random locations; and
labeling and supplying the training set to the three-way CNN to train the three-way CNN.

29. The method of claim 28, further comprising:
generating a first confidence map with the three-way CNN that shows the probability of a pixel being on the lumen-intima interface;
generating a second confidence map with the three-way CNN that shows the probability of a pixel being on the media-adventitia interface;
searching each confidence map for rows with a maximum response for each of the lumen-intima interface and the media-adventitia interface, thereby obtaining an n-pixel thick boundary for the lumen-intima interface and an n-pixel thick boundary for the media-adventitia interface.

30. The method of claim 29, further comprising refining the boundaries using two active contour models, the two active contour models creating two open snakes, wherein the refining comprises:
initializing the two open snakes, one for each n-pixel thick boundary for the lumen-intima interface and the media-adventitia interface;
deforming the two open snakes based on a probability map generated by the three-way CNN; and
determining intima-media thickness as an average of a vertical distance between the two open snakes.

31. The method of claim 17, wherein the method further comprises obtaining an ultrasound video of the wall of the artery of the subject.

32. The method of claim 1, wherein the method further comprises obtaining an ultrasound video of the wall of the artery of the subject.

* * * * *